US 10,567,890 B2

(12) United States Patent
Meier et al.

(10) Patent No.: US 10,567,890 B2
(45) Date of Patent: *Feb. 18, 2020

(54) AUDIO ACCESSORY FOR AUDITORY PROSTHESIS SYSTEM THAT INCLUDES BODY-WORN SOUND PROCESSOR APPARATUS

(71) Applicant: ADVANCED BIONICS AG, Staefa (CH)

(72) Inventors: Roger S. Meier, Canyon County, CA (US); Logan P. Palmer, Santa Monica, CA (US); Diane H. Chang, Arcadia, CA (US); Thomas P. Walsh, Valencia, CA (US)

(73) Assignee: Advanced Bionics AG, Staefa (CH)

( * ) Notice: Subject to any disclaimer, the term of this patent is extended or adjusted under 35 U.S.C. 154(b) by 0 days.

This patent is subject to a terminal disclaimer.

(21) Appl. No.: 16/370,989

(22) Filed: Mar. 30, 2019

(65) Prior Publication Data

US 2019/0230452 A1    Jul. 25, 2019

Related U.S. Application Data

(63) Continuation of application No. 15/547,488, filed as application No. PCT/US2015/013807 on Jan. 30, 2015, now Pat. No. 10,277,993.

(51) Int. Cl.
*H04R 25/00* (2006.01)
*A61N 1/05* (2006.01)
(Continued)

(52) U.S. Cl.
CPC ......... *H04R 25/554* (2013.01); *A61N 1/0541* (2013.01); *A61N 1/36036* (2017.08);
(Continued)

(58) Field of Classification Search
CPC ............ A61N 1/36038; A61N 1/37229; A61N 1/36036; A61N 1/3787; G10L 21/0216;
(Continued)

(56) References Cited

U.S. PATENT DOCUMENTS 7,860,572 B2   12/2010   Ibrahim
7,995,771 B1   8/2011    Faltys et al.
(Continued)

FOREIGN PATENT DOCUMENTS

CN     103416076    11/2013
EP      2671392      8/2012
(Continued)

OTHER PUBLICATIONS

International Search Report and Written Opinion received in International Application No. PCT/US15/013807, dated Nov. 5, 2015.
(Continued)

*Primary Examiner* — Brian Ensey
(74) *Attorney, Agent, or Firm* — ALG Intellectual Property, LLC

(57) ABSTRACT

An exemplary auditory prosthesis system for a patient includes a body-worn sound processor apparatus configured to control an operation of a cochlear implant, a headpiece configured to facilitate wireless coupling of the body-worn sound processor apparatus to the cochlear implant, an audio accessory that includes a microphone configured to receive incoming audio and convert the incoming audio into an audio signal, a first communication port configured to connect directly to a communication port of the body-worn sound processor apparatus by way of a first cable, a second communication port configured to connect directly to a communication port of the headpiece by way of a second cable, and a control module communicatively coupled to the microphone and the first and second communication ports
(Continued)

and that is configured to provide the audio signal to the body-worn sound processor apparatus by way of the first cable.

20 Claims, 6 Drawing Sheets

(51) Int. Cl.
*A61N 1/36* (2006.01)
*A61N 1/372* (2006.01)
*G10L 21/0216* (2013.01)
H04R 25/04 (2006.01)
A61N 1/378 (2006.01)

(52) U.S. Cl.
CPC ..... *A61N 1/36038* (2017.08); *A61N 1/37229* (2013.01); *G10L 21/0216* (2013.01); *H04R 25/55* (2013.01); *H04R 25/606* (2013.01); A61N 1/3787 (2013.01); G10L 2021/02166 (2013.01); H04R 25/04 (2013.01); H04R 25/405 (2013.01); H04R 25/556 (2013.01); H04R 25/558 (2013.01); H04R 2225/67 (2013.01); H04R 2460/01 (2013.01)

(58) Field of Classification Search
CPC ........ G10L 2021/02166; H04R 25/554; H04R 25/55; H04R 25/558; H04R 25/556; H04R 25/04; H04R 2225/67
See application file for complete search history.

(56) References Cited

U.S. PATENT DOCUMENTS

| | | |
|---|---|---|
| 8,503,685 B2* | 8/2013 | Kulkarni ................ H04R 1/406 381/60 |
| 2005/0010267 A1 | 1/2005 | Ibrahim |
| 2005/0209657 A1 | 9/2005 | Chung et al. |
| 2007/0016267 A1 | 1/2007 | Griffin et al. |
| 2012/0041515 A1* | 2/2012 | Meskens ............ A61N 1/37229 607/57 |
| 2014/0025138 A1 | 1/2014 | Meskens et al. |
| 2014/0233775 A1 | 8/2014 | Hartley et al. |

FOREIGN PATENT DOCUMENTS

| | | |
|---|---|---|
| WO | 2012/106206 | 8/2012 |
| WO | 2013/165361 | 11/2013 |

OTHER PUBLICATIONS

Non-Final Office Action received in U.S. Appl. No. 15/547,488 dated Aug. 9, 2018.

* cited by examiner

AUDIO ACCESSORY FOR AUDITORY PROSTHESIS SYSTEM THAT INCLUDES BODY-WORN SOUND PROCESSOR APPARATUS

RELATED APPLICATIONS

The present application is a continuation application of U.S. patent application Ser. No. 15/547,488, filed Jul. 29, 2017, which application is a U.S. National Stage Entry of PCT Application No. PCT/US2015/013807, filed Jan. 30, 2015. The contents of these applications are incorporated herein by reference in their respective entireties.

BACKGROUND INFORMATION

Many auditory prosthesis systems are capable of implementing noise-cancelation processing (e.g., beamforming) that improves the hearing performance of certain patients with hearing loss. For example, an auditory prosthesis system may include a behind-the-ear ("BTE") sound processor unit located behind the ear of a patient. In this example, the BTE sound processor unit may include multiple microphones used to perform beamforming operations that remove unwanted noise from incoming audio.

Unfortunately, other types of sound processor units may be unable to perform such noise-cancelation processing. For example, certain body-worn sound processor units may not have beamforming capabilities. Despite this deficiency, some patients may still choose a body-worn sound processor unit over a BTE sound processor unit for various reasons. As an example, some patients may need to use a body-worn sound processor unit to support the power requirements of older-generation cochlear implants. Additionally or alternatively, some patients may prefer a body-worn sound processor unit due to certain water-proofing benefits not yet available in BTE sound processor units. Accordingly, these patients may be unable to achieve the improved hearing performance afforded by beamforming operations due to their choice to use a conventional body-worn sound processor unit.

BRIEF DESCRIPTION OF THE DRAWINGS

The accompanying drawings illustrate various embodiments and are a part of the specification. The illustrated embodiments are merely examples and do not limit the scope of the disclosure. Throughout the drawings, identical or similar reference numbers designate identical or similar elements.

DETAILED DESCRIPTION

Figure 1:
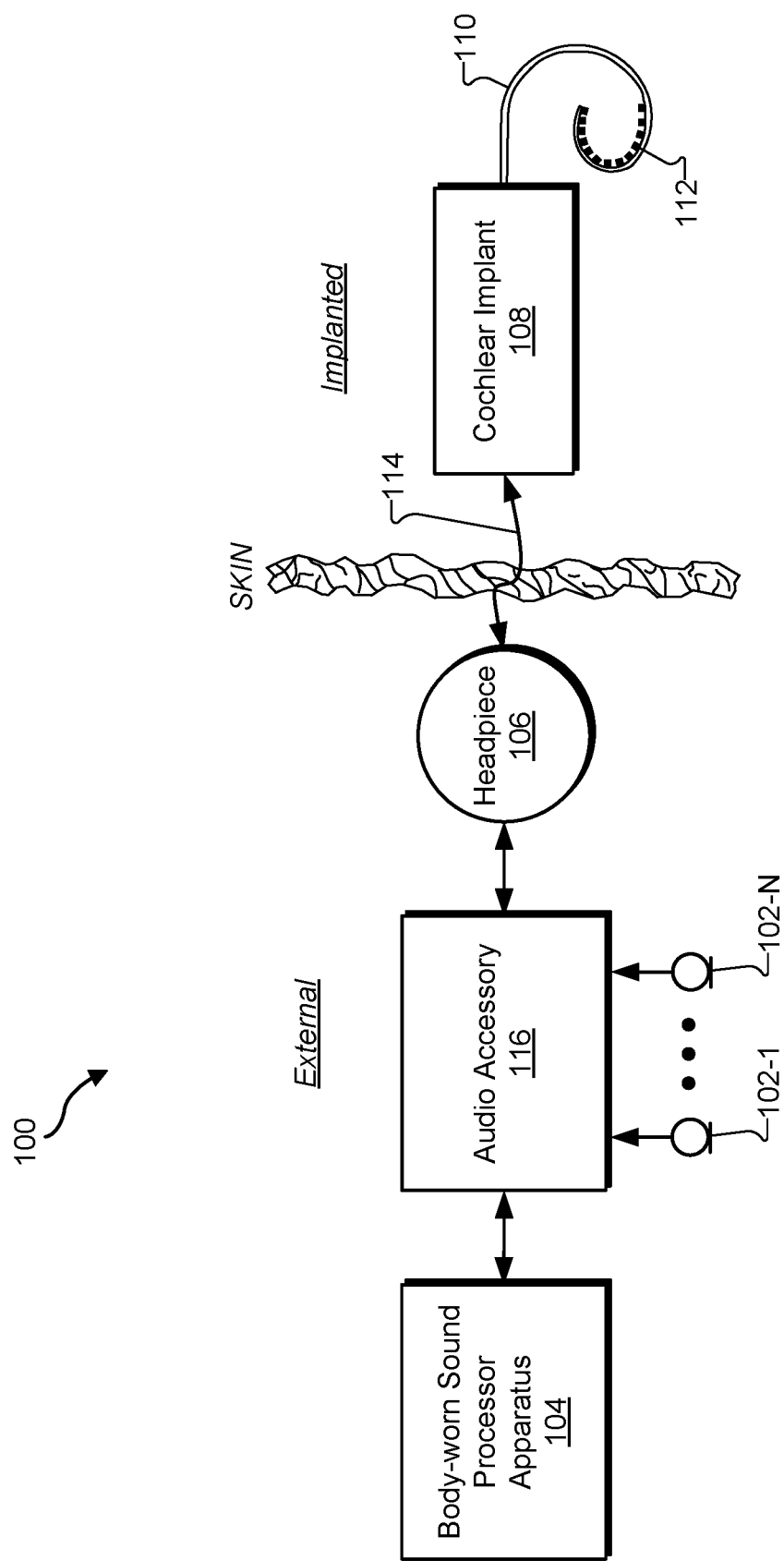
FIG. 1 illustrates an exemplary auditory prosthesis system according to principles described herein.

Auditory prosthesis systems are described herein. As will be described below, an exemplary auditory prosthesis system may include 1) a body-worn sound processor apparatus configured to be external to a patient and control an operation of a cochlear implant implanted within the patient, 2) a headpiece configured to be external to the patient and facilitate wireless coupling of the body-worn sound processor apparatus to the cochlear implant, and 3) an audio accessory configured to be external to the patient. In one example, the audio accessory may include a plurality of microphones that receive incoming audio and convert the incoming audio into a plurality of audio signals. In this example, the audio accessory may also include a first communication port that connects directly to a communication port of the body-worn sound processor apparatus by way of a first cable and a second communication port that connects directly to a communication port of the headpiece by way of a second cable. The communication port of the body-worn sound processor apparatus may have been designed specifically for interfacing the body-worn sound processor apparatus with the headpiece. Similarly, the communication port of the headpiece may have been designed specifically for interfacing the headpiece with the body-worn sound processor apparatus.

In one example, the audio accessory may further include a control module that generates a processed audio signal by processing the plurality of audio signals converted by the plurality of microphones from the incoming audio (e.g., using a beamforming operation) and then provides the processed audio signal to the body-worn sound processor apparatus. By providing the processed audio signal to the body-worn sound processor apparatus in this way, the audio accessory may enable the body-worn sound processor to generate a control parameter that controls the operation of the cochlear implant and then transmit, by way of the first and second cables and the first and second communication ports, the control parameter to the headpiece for wireless transmission to the cochlear implant.

As a specific example, a cochlear implant patient may use a conventional body-worn sound processor apparatus that lacks beamforming capabilities. On the one hand, the patient may want to continue using the conventional body-worn sound processor apparatus for one or more reasons (e.g., cost, power requirements, and/or water-proofing benefits) instead of transitioning to a BTE sound processor apparatus that may be capable of performing beamforming. On the other hand, the patient may want to improve his or her hearing performance by implementing certain beamforming operations that, for example, remove unwanted noise from incoming audio. In view of these considerations, the patient may interpose an audio accessory that provides beamforming capabilities between the conventional body-worn sound processor apparatus and a conventional headpiece that facilitates wireless coupling of the body-worn sound processor apparatus to the cochlear implant. By interposing the audio accessory in this way, the patient may be able to achieve the beamforming benefits provided by the audio accessory while continuing to use the conventional body-worn sound processor apparatus.

In one example, the patient may interpose the audio accessory between the conventional body-worn sound processor apparatus and the conventional headpiece by unplugging a conventional radio-frequency ("RF") cable from a communication port of the conventional headpiece. In this example, the communication port of the conventional headpiece may be designed to interface the conventional headpiece with the conventional body-worn sound processor apparatus via the conventional RF cable. Similarly, the conventional RF cable may be designed to connect the conventional body-worn sound processor apparatus and the conventional headpiece to one another. Upon unplugging the conventional RF cable from the conventional headpiece, the patient may insert the unplugged terminal of the conventional RF cable into a first communication port of the audio accessory. By inserting the unplugged terminal of the conventional RF cable into the first communication port of the audio accessory in this way, the patient may connect the first communication port of the audio accessory directly to the communication port of the conventional body-worn sound processor apparatus (even though the communication port of the conventional body-worn sound processor apparatus is designed to interface the conventional body-worn sound processor apparatus directly with the conventional headpiece).

Continuing with this example, the patient may also insert one terminal of another RF cable into a second communication port of the audio accessory and another terminal of the other RF cable into the communication port of the conventional headpiece. By inserting the terminals of the other RF cable into these communication ports in this way, the patient may connect the second communication port of the audio accessory directly to the communication port of the conventional headpiece (even though the communication port of the conventional headpiece is designed to interface the conventional headpiece directly with the conventional body-worn sound processor apparatus).

Accordingly, and as will be described in more detail below, the audio accessory may essentially create a bridge and/or relay between the conventional body-worn sound processor and the conventional headpiece that facilitates beamforming capabilities for the conventional body-worn sound processor apparatus, thereby potentially improving the patient's overall hearing performance.

FIG. 1 illustrates an exemplary auditory prosthesis system 100. As shown, auditory prosthesis system 100 may include various components configured to be located external to a patient including, but not limited to, an audio accessory 116 that includes a plurality of microphones 102-1 through 102-N (collectively referred to herein as "microphones 102"), a body-worn sound processor apparatus 104, and a headpiece 106. Auditory prosthesis system 100 may further include various components configured to be implanted within the patient including, but not limited to, a cochlear implant 108 and a lead 110 with a plurality of electrodes 112 disposed thereon. As will be described in more detail below, additional or alternative components may be included within auditory prosthesis system 100 as may serve a particular implementation. The components shown in FIG. 1 will now be described in more detail.

Microphones 102 may be configured to detect incoming audio presented to the patient. Microphones 102 may be implemented in any suitable manner. For example, microphones 102 may include and/or represent microphones that are configured to be placed within the concha of the ear near the entrance to the ear canal, such as a T-MIC™ microphone from Advanced Bionics. Such microphones may be held within the concha of the ear near the entrance of the ear canal by a boom or stalk that is attached to an ear hook configured to be selectively attached to audio accessory 116. Additionally or alternatively, microphones 102 may be implemented by one or more microphones disposed on top of audio accessory 116, one or more microphones disposed within audio accessory 116, combinations of one or more of the same, and/or any other suitable microphones as may serve a particular implementation. In some embodiments, audio accessory 116 may additionally or alternatively include a telecoil configured to detect the incoming audio presented to the patient. In these embodiments, audio accessory 116 may process the audio detected by the telecoil in any of the ways described herein.

In some examples, microphones 102 may convert the incoming audio into a plurality of audio signals. For example, microphone 102-1 may convert the incoming audio into a first audio signal representative of the incoming audio from the perspective and/or positioning of microphone 102-1. In this example, microphone 102-N may convert the same incoming audio into a second audio signal representative of the incoming audio from the perspective and/or positioning of microphone 102-N.

Audio accessory 116 may be configured to removably attach to the ear of the patient. Audio accessory 116 may be implemented in any suitable manner. For example, audio accessory 116 may include and/or represent a BTE unit that is configured to wrap around and/or sit atop of the ear. In this example, audio accessory 116 may include and/or represent various computing and/or electrical components that facilitate certain processing and/or communication functionalities within auditory prosthesis system 100. In particular, audio accessory 116 may include and/or represent computing and/or electrical components found in certain receiver-in-the-canal hearing aids. Accordingly, audio accessory 116 may include and/or be implemented by multiple microphones, wireless communication transceivers, analog-to-digital converters (ADCs), digital signal processors, digital-to-analog converters (DACs), combinations of one or more of the same, and/or any other suitable computing and/or electrical components as may serve a particular implementation.

In some examples, audio accessory 116 may process the plurality of audio signals converted by microphones 102 from the incoming audio. In one example, audio accessory 116 may generate a processed audio signal by processing the plurality of audio signals converted by microphones 102. For example, audio accessory 116 may perform a beamforming operation on the plurality of audio signals to remove unwanted noise. The term "beamforming," as used herein, generally refers to any type or form of signal processing technique, feature, and/or mechanism that filters noise by applying constructive and/or destructive interference in specific directions relative to the source of the noise. As another example, audio accessory 116 may process the audio signals converted by microphones 102 by performing one or more sound processing operations on the audio signals that the body-worn sound processor apparatus 104 is not capable of performing. In this manner, audio accessory 116 may provide additional sound processing capabilities for older generation processors. As another example, audio accessory 116 may process the audio signals by mixing streaming audio with the audio signals. The streaming audio may originate at any suitable source (e.g., via an auxiliary input port included in the audio accessory 116).

Upon generating the processed audio signal, audio accessory 116 may provide the processed audio signal to body-worn sound processor apparatus 104 to facilitate further processing and/or generation of a control parameter that controls an operation of cochlear implant 108.

Additionally or alternatively, audio accessory 116 may provide wireless connectivity to auditory prosthesis system 100. For example, audio accessory 116 may facilitate wireless communication between auditory prosthesis system 100 and one or more other computing devices by way of a BLUETOOTH or hearing instrument body area network (HiBAN) connection. By facilitating wireless communication in this way, audio accessory 116 may enable body-worn sound processor apparatus 104, headpiece 106, and/or cochlear implant 108 to create and/or modify one or more settings, operations, and/or parameters that improve the hearing performance of the patient and/or provide additional comfort and/or convenience to the patient.

Body-worn sound processor apparatus 104 may be configured to be worn off the ear of the patient. Body-worn sound processor apparatus 104 may be implemented in any suitable manner. In some examples, body-worn sound processor apparatus 104 may be worn or carried by the patient at any location other than behind or on the ear. For example, body-worn sound processor apparatus 104 may be secured to a piece of clothing worn by the patient, carried in a pocket or pouch, and/or otherwise carried by the patient. Because body-worn sound processor apparatus 104 is not worn behind or on the ear, body-worn sound processor apparatus 104 may be relatively larger than typical BTE sound processors and may therefore include additional or enhanced features compared to such typical BTE sound processors. For example, body-worn sound processor apparatus 104 may be coupled to one or more accessory headers each providing one or more additional features and/or capabilities to body-worn sound processor apparatus 104. In some examples, body-worn sound processor apparatus 104 may be water proof or at least water resistant.

In some examples, body-worn sound processor apparatus 104 may lack certain noise-cancelation capabilities. For example, body-worn sound processor apparatus 104 may be unable to perform beamforming operations since body-worn sound processor apparatus 104 does not include multiple ear-level microphones. Additionally or alternatively, body-worn sound processor apparatus 104 may be unable to provide wireless connectivity to auditory prosthesis system 100 since body-worn sound processor apparatus 104 does not offer optimal placement for certain antennae that facilitate wireless communication. Accordingly, auditory prosthesis system 100 may rely on audio accessory 116 to address these deficiencies of body-worn sound processor apparatus 104 by providing certain beamforming capabilities and/or wireless connectivity.

In some examples, body-worn sound processor apparatus 104 may generate certain control parameters that control an operation of cochlear implant 108. For example, body-worn sound processor apparatus 104 may receive the processed audio signal from audio accessory 116. Upon receiving the processed audio signal, body-worn sound processor apparatus 104 may generate a control parameter that controls an operation of cochlear implant 108 based at least in part on the processed audio signal. Body-worn sound processor apparatus 104 may then transmit the control parameter to headpiece 106 for wireless transmission to cochlear implant 108.

The term "control parameter," as used herein, generally refers to any type or form of parameter, instruction, and/or communication that governs and/or modifies an operation of a cochlear implant. Exemplary control parameters include, but are not limited to, volume control parameters, microphone sensitivity parameters, program selection parameters, noise reduction parameters, microphone direction parameters, pitch parameters, timbre parameters, sound quality parameters, most comfortable current levels ("M levels"), threshold current levels, channel acoustic gain parameters, front and backend dynamic range parameters, current steering parameters, pulse rate values, pulse width values, frequency parameters, amplitude parameters, waveform parameters, electrode polarity parameters (i.e., anode-cathode assignment), location parameters (i.e., which electrode pair or electrode group receives the stimulation current), stimulation type parameters (i.e., monopolar, bipolar, or tripolar stimulation), burst pattern parameters (e.g., burst on time and burst off time), duty cycle parameters, spectral tilt parameters, filter parameters, dynamic compression parameters, variations of one or more of the same, combinations of one or more of the same, or any other suitable control parameters.

In some examples, body-worn sound processor apparatus 104 may wirelessly transmit control parameters (e.g., in the form of data words included in a forward telemetry sequence) and/or power signals to cochlear implant 108 by way of a wireless communication link 114 between headpiece 106 and cochlear implant 108. It will be understood that wireless communication link 114 may include a bi-directional communication link and/or one or more dedicated uni-directional communication links.

Headpiece 106 may be communicatively coupled to body-worn sound processor apparatus 104 and may include an external antenna (e.g., a coil and/or one or more wireless communication components) configured to facilitate selective wireless coupling of sound processor apparatus 104 to cochlear implant 108. Headpiece 106 may be implemented in any suitable manner. In one example, headpiece 106 may be used to selectively and wirelessly couple any other external device to cochlear implant 108. To this end, headpiece 106 may be configured to be affixed to the patient's head and positioned such that the external antenna housed within headpiece 106 is communicatively coupled to a corresponding implantable antenna (which may also be implemented by a coil and/or one or more wireless communication components) included within or otherwise associated with cochlear implant 108. In this manner, stimulation parameters and/or power signals may be wirelessly transmitted between sound processor apparatus 104 and cochlear implant 108 via a wireless communication link 114 (which may include a bi-directional communication link and/or one or more dedicated uni-directional communication links as may serve a particular implementation).

Cochlear implant 108 may include any type of implantable stimulator that may be used in association with the systems and methods described herein. Cochlear implant 108 may be implemented in any suitable manner. For example, cochlear implant 108 may be implemented by an implantable cochlear stimulator. In some alternative implementations, cochlear implant 108 may include a brainstem implant and/or any other type of cochlear implant that may be implanted within a patient and configured to apply stimulation to one or more stimulation sites located along an auditory pathway of a patient.

In some examples, cochlear implant 108 may be configured to generate electrical stimulation representative of an audio signal processed by body-worn sound processor apparatus 104 (e.g., the processed audio signal received from audio accessory 116) in accordance with one or more control parameters transmitted thereto by body-worn sound processor apparatus 104. Cochlear implant 108 may be further configured to apply the electrical stimulation to one or more stimulation sites within the patient via one or more electrodes 112 disposed along lead 110. In some examples, cochlear implant 108 may include a plurality of independent current sources each associated with a channel defined by one or more of electrodes 112. In this manner, different stimulation current levels may be applied to multiple stimulation sites simultaneously by way of multiple electrodes 112.

The auditory prosthesis system 100 illustrated in FIG. 1 may be referred to as a cochlear implant system because body-worn sound processor apparatus 104 is configured to direct cochlear implant 108 to generate and apply electrical stimulation representative of audio content (e.g., one or more audio signals) to one or more stimulation sites within the patient by way of one or more of electrodes 112. Auditory prosthesis system 100 may alternatively be implemented by an electro-acoustic stimulation ("EAS") system configured to provide both electrical stimulation by way of cochlear implant 108 and acoustic stimulation by way of a receiver or loudspeaker (not shown) connected to body-worn sound processor apparatus 104.

Figure 2:
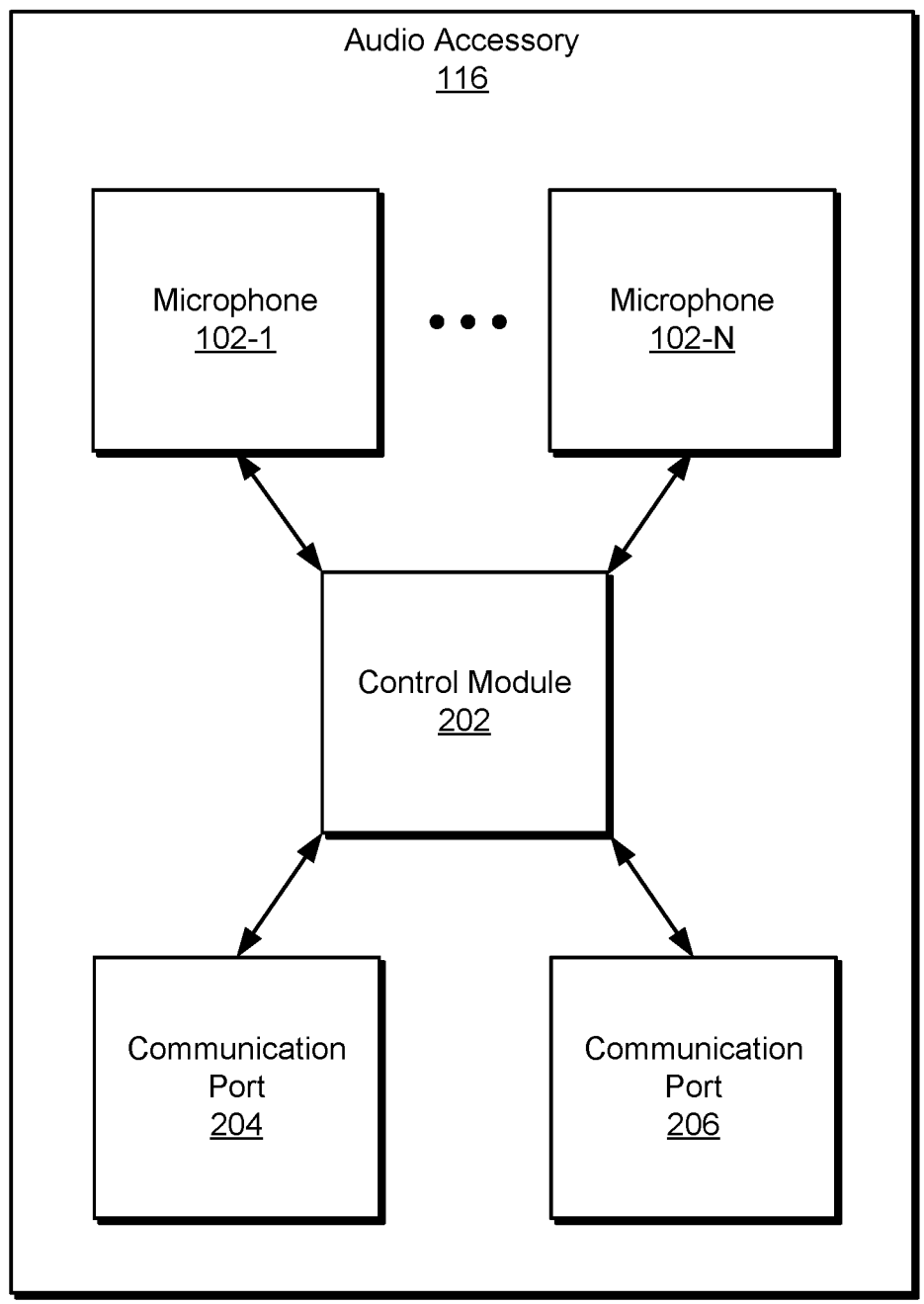
FIG. 2 illustrates exemplary components that may be included within an audio accessory according to principles described herein.

FIG. 2 illustrates exemplary components that may be included within audio accessory 116. As shown, audio accessory 116 may include microphones 102, a control module 202, a communication port 204, and a communication port 206. It will be recognized that audio accessory 116 may include additional or alternative components as may serve a particular implementation. For example, audio accessory 116 may include an optional wireless communication port configured to facilitate wireless communication between audio accessory 116 and body-worn sound processor apparatus 104. In some examples, one or more of the components included in audio accessory 116 (e.g., microphones 102, control module 202, communication port 204, and communication port 206) may be housed within and/or disposed on a single casing.

Control module 202 may be communicatively coupled to microphones 102 within audio accessory 116. The communicative coupling between control module 202 and microphones 102 may be implemented in any suitable manner. Control module 202 may be configured to interact with and/or receive audio signals from microphones 102 within audio accessory 116.

In some examples, control module 202 may be configured to perform one or more operations with respect to one or more components connected to or otherwise communicatively coupled to audio accessory 116. For example, control module 202 may be configured to process a plurality of audio signals converted by microphones 102 from incoming audio. In particular, control module 202 may obtain the plurality of audio signals from microphones 102 and then perform a beamforming operation on the plurality of audio signals. The beamforming operation may involve generating a processed audio signal that excludes certain unwanted noise included in the plurality of audio signals. Upon performing the beamforming operation, control module 202 may provide the processed audio signal to body-worn sound processor apparatus 104 by way of a first cable that connects communication port 204 directly to a communication port of body-worn sound processor apparatus 104.

Control module 202 may be implemented by any suitable combination of integrated circuits, circuitry, processors, and/or computing devices configured to perform one or more of the operations and/or functions described herein. Exemplary implementations of control module 202 will be described below.

Communication port 204 may be configured to connect directly to a communication port of body-worn sound processor apparatus 104 by way of the first cable. Communication port 204 may be implemented in any suitable manner. For example, communication port 204 may include and/or represent an RF port that enables audio accessory 116 to provide the processed audio signal to body-worn sound processor apparatus 104. In this example, communication port 204 may include and/or represent a female connection receptacle that receives and/or accepts a male connection terminal of the first cable to establish the connection between audio accessory 116 and body-worn sound processor apparatus 104. Additionally or alternatively, communication port 204 may include and/or represent a male connection terminal or hybrid fastener that fastens to a female connection receptacle or hybrid fastener of the second cable to establish the connection between audio accessory 116 and body-worn sound processor apparatus 104.

Similarly, communication port 206 may be configured to connect directly to a communication port of headpiece 106 by way of a second cable. Communication port 206 may be implemented in any suitable manner. For example, communication port 206 may include and/or represent an RF port that enables audio accessory 116 to transmit and/or relay a control parameter that controls an operation of cochlear implant 108. In this example, communication port 206 may include and/or represent a female connection receptacle that receives and/or accepts a male connection terminal of the second cable to establish the connection between audio accessory 116 and headpiece 106. Additionally or alternatively, communication port 206 may include and/or represent a male connection terminal or hybrid fastener that fastens to a female connection receptacle or hybrid fastener of the second cable to establish the connection between audio accessory 116 and headpiece 106.

Microphones 102, control module 202, communication port 204, and communication port 206 may be implemented in any suitable manner to facilitate noise-cancelation for body-worn sound processor apparatus 104 and/or relay control parameters from body-worn sound processor apparatus 104 to cochlear implant 108 by way of the first and second cables and communication ports 204 and 206.

Figure 3:
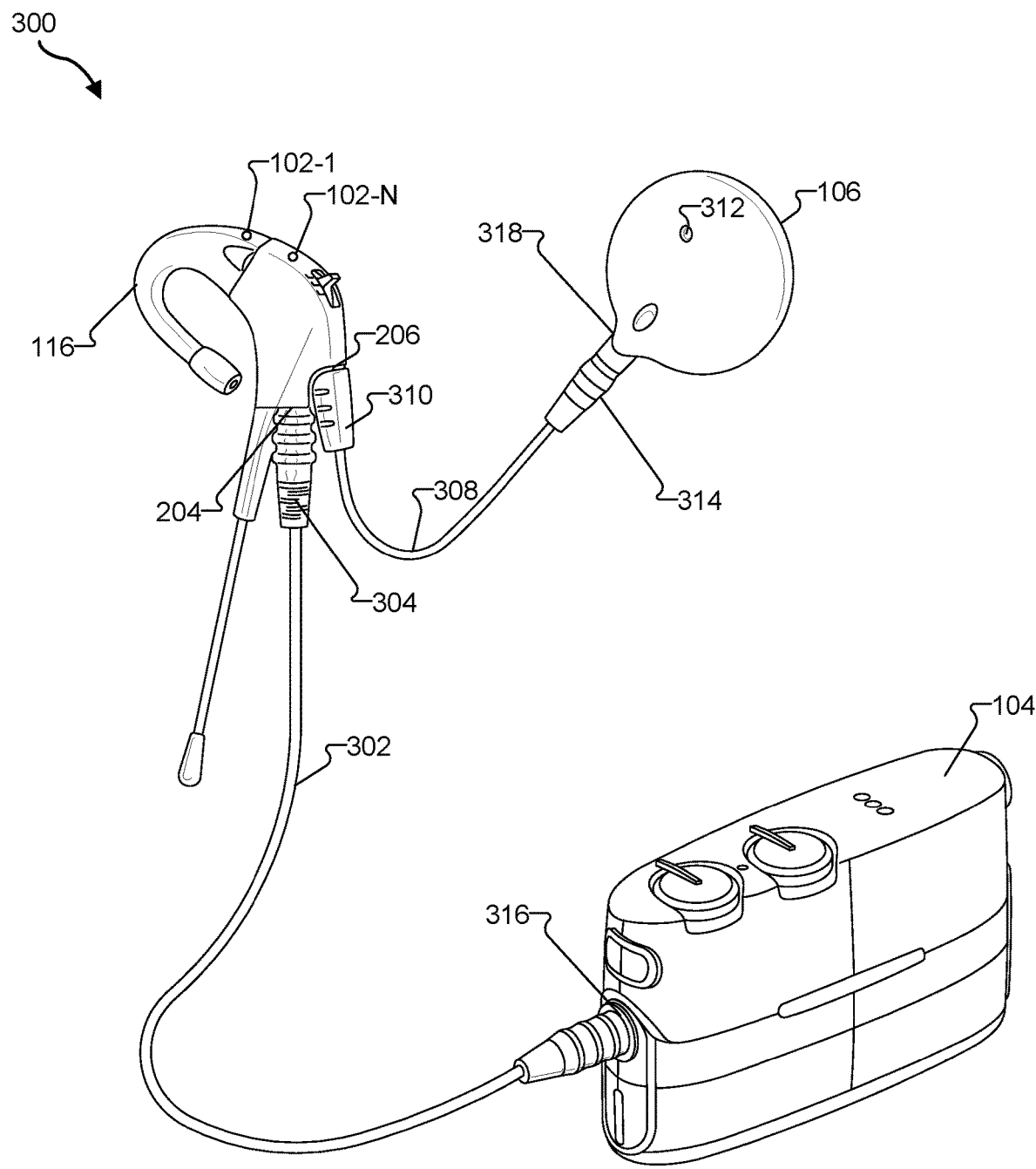
FIG. 3 shows an exemplary implementation of the auditory prosthesis system of FIG. 1 with an audio accessory being interposed between a body-worn sound processor apparatus and a headpiece according to principles described herein.

FIG. 3 shows an exemplary implementation 300 of auditory prosthesis system 100 with audio accessory 116 being interposed between body-worn sound processor apparatus 104 and headpiece 106. As shown in FIG. 3, exemplary implementation 300 may include body-worn sound processor apparatus 104 configured to be external to a patient. In this example, body-worn sound processor apparatus 104 may control an operation of a cochlear implant (not shown) implanted within the patient.

In one example, exemplary implementation 300 may also include headpiece 106 configured to be external to the patient. In this example, headpiece 106 may facilitate wireless coupling of body-worn sound processor apparatus 104 to the cochlear implant. Headpiece 106 may include a microphone 312 designed to convert incoming audio into audio signals used to generate control parameters that control operations of the cochlear implant. In other words, microphone 312 may have been intended (during the design and/or manufacture of headpiece 106) to convert incoming audio into such audio signals.

In one example, exemplary implementation 300 may further include audio accessory 116 configured to be external to the patient. In this example, audio accessory 116 may include microphones 102-1 and 102-N that receive incoming audio and/or convert the incoming audio into a plurality of audio signals. In exemplary implementation 300, microphones 102-1 and 102-N may effectively replace microphone 312 included in headpiece 106 such that audio signals converted from incoming audio by microphone 312 are no longer used to generate control parameters that control operations of the cochlear implant.

Additionally or alternatively, audio accessory 116 may include communication port 204 that connects directly to a communication port 316 of body-worn sound processor apparatus 104 by way of a cable 302. Communication port 316 of body-worn sound processor apparatus 104 may be designed to interface and/or connect body-worn sound processor apparatus 104 directly with and/or to headpiece 106. In other words, although communication port 316 connects body-worn sound processor apparatus 104 directly to communication port 204 of audio accessory 116 in exemplary implementation 300, communication port 316 may have been intended (during the design and/or manufacture of body-worn sound processor apparatus 104) to connect body-worn sound processor apparatus 104 directly to headpiece 106.

In one example, audio accessory 116 may include communication port 206 that connects directly to a communication port 318 by way of a cable 308. Communication port 318 may be designed to interface and/or connect headpiece 106 directly with and/or to body-worn sound processor apparatus 104. In other words, although communication port 318 connects headpiece 106 directly to communication port 206 of audio accessory 116 in exemplary implementation 300, communication port 318 may have been intended (during the design and/or manufacture of headpiece 106) to connect headpiece 106 directly to body-worn sound processor apparatus 104.

As an example in connection with FIG. 3, control module 202 included within audio accessory 116 may obtain a plurality of audio signals converted by microphones 102-1 and 102-N from incoming audio presented to the patient. Upon obtaining the plurality of audio signals, control module 202 may generate a processed audio signal by processing the plurality of audio signals and/or performing a beamforming operation on the plurality of audio signals. Control module 202 may then provide the processed audio signal to body-worn sound processor apparatus 104 by way of cable 302.

In this example, body-worn sound processor apparatus 104 may receive the processed audio signal from audio accessory 116 by way of cable 302. Upon receiving the processed audio signal, body-worn sound processor apparatus 104 may generate a control parameter that controls an operation of the cochlear implant based at least in part on the processed audio signal. Body-worn sound processor apparatus 104 may then transmit the control parameter to audio accessory 116 by way of cable 302 and communication port 204.

Continuing with this example, audio accessory 116 may receive the control parameter at communication port 204 from body-worn sound processor apparatus 104 by way of cable 302. Audio accessory 116 may then relay the control parameter by transmitting the control parameter from communication port 206 to headpiece 106 by way of cable 308. Upon receiving the control parameter from audio accessory 116, headpiece 106 may pass the control parameter to the cochlear implant by way of wireless transmission.

Figure 4:
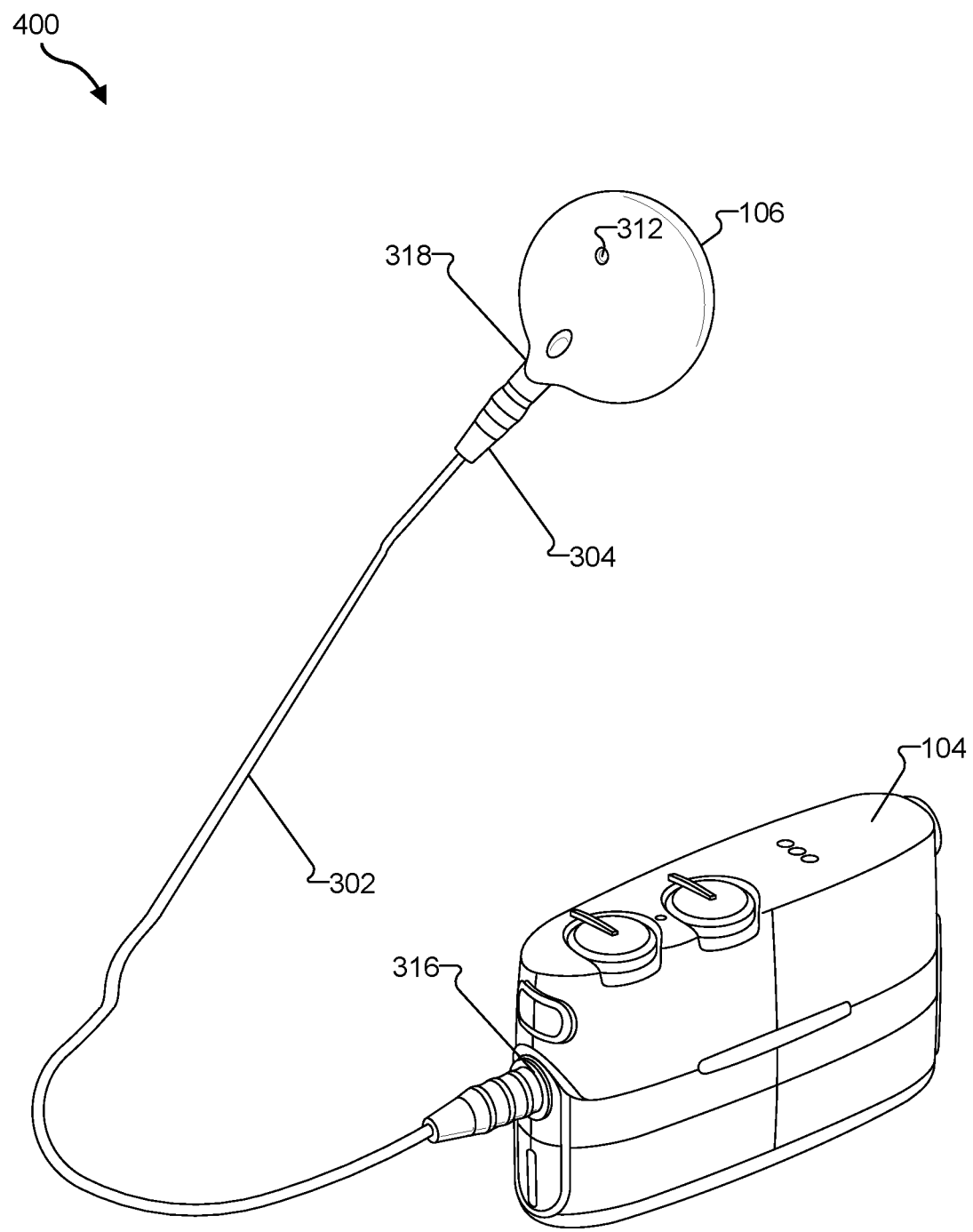
FIG. 4 shows an exemplary implementation of certain components of the auditory prosthesis system of FIG. 1 without an audio accessory being interposed between a body-worn sound processor apparatus and a headpiece according to principles described herein.

FIG. 4 shows an exemplary implementation 400 of certain components of auditory prosthesis system 100 without audio accessory 116 being interposed between body-worn sound processor apparatus 104 and headpiece 106. As shown in FIG. 4, exemplary implementation 400 may include body-worn sound processor apparatus 104 configured to be external to a patient. In this example, body-worn sound processor apparatus 104 may control an operation of a cochlear implant (not shown) implanted within the patient.

In one example, exemplary implementation 400 may also include headpiece 106 configured to be external to the patient. In this example, headpiece 106 may facilitate wireless coupling of body-worn sound processor apparatus 104 to the cochlear implant. Headpiece 106 may include a microphone 312 that converts incoming audio into audio signals used to generate control parameters that control operations of the cochlear implant. Since exemplary implementation 400 excludes audio accessory 116, microphone 312 may be used as intended (during the design and/or manufacture of headpiece 106) to convert incoming audio into such audio signals. Accordingly, exemplary implementation 400 may represent and/or demonstrate the originally intended configuration of an auditory prosthesis system that includes body-worn sound processor apparatus 104 and headpiece 106.

As shown in FIG. 4, cable 302 may be used to establish a direct connection between body-worn sound processor apparatus 104 and headpiece 106. Alternatively, cable 308 may be used to establish a direct connection between body-worn sound processor apparatus 104 and headpiece 106.

In one example, body-worn sound processor apparatus 104 may lack certain beamforming capabilities. Despite this deficiency, the patient may want to continue using body-worn sound processor apparatus 104 for one or more reasons (e.g., cost, power requirements, and/or water-proofing benefits) instead of transitioning to a BTE sound processor apparatus. On the other hand, the patient may want to improve his or her hearing performance by implementing certain beamforming operations that remove unwanted noise from incoming audio. As a result of these considerations, the patient may removably interpose audio accessory 116 between body-worn sound processor apparatus 104 and headpiece 106 in exemplary implementation 400 to achieve exemplary implementation 300. By removably interposing audio accessory 116 in this way, the patient may be able to achieve the beamforming benefits provided by audio accessory 116 while continuing to use body-worn sound processor apparatus 104.

In one example, the patient may removably interpose audio accessory 116 between body-worn sound processor apparatus 104 and headpiece 106 by unplugging terminal 304 of cable 302 from communication port 318 of headpiece 106. Upon unplugging terminal 304 of cable 302 from communication port 318, the patient may insert terminal 304 into communication port 204 of audio accessory 116. By inserting terminal 304 of cable 302 into communication port 204 in this way, the patient may connect communication port 204 of audio accessory 116 directly to communication port 316 of body-worn sound processor apparatus 104 (even though communication port 316 is designed to interface body-worn sound processor apparatus 104 directly with headpiece 106).

Continuing with this example, the patient may obtain cable 308 and then insert terminal 310 of cable 308 into communication port 206 of audio accessory 116 and terminal 314 of cable 308 into communication port 318 of headpiece 106. By inserting terminals 310 and 314 of cable 308 into communication ports 206 and 318, respectively, the patient may connect communication port 206 of audio accessory 116 directly to communication port 318 of headpiece 106 (even though communication port 318 is designed to interface headpiece 106 directly with body-worn sound processor apparatus 104).

Figure 5:
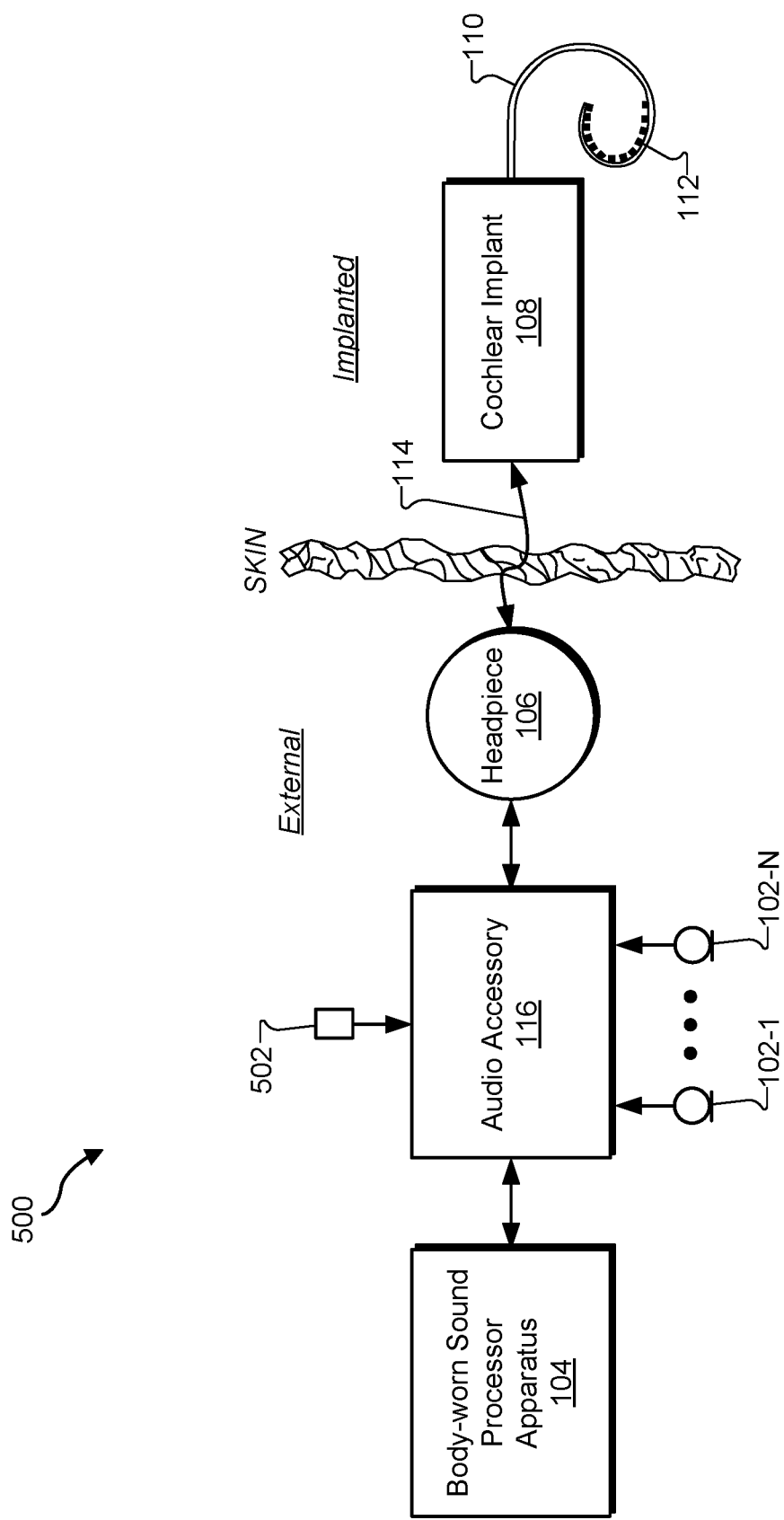
FIG. 5 illustrates an exemplary auditory prosthesis system according to principles described herein.

FIG. 5 illustrates an exemplary auditory prosthesis system 500. As shown, auditory prosthesis system 500 may include various components configured to be located external to a patient including, but not limited to, audio accessory 116 that includes microphones 102 and an auxiliary audio input 502, body-worn sound processor apparatus 104, and headpiece 106. Auditory prosthesis system 500 may further include various components configured to be implanted within the patient including, but not limited to, cochlear implant 108 and lead 110 with electrodes 112 disposed thereon.

Auxiliary audio input 502 may be configured to receive incoming audio from an audio source. Auxiliary audio input 502 may be implemented in any suitable manner. For example, auxiliary audio input 502 may include and/or represent a female audio input port and/or jack that receives and/or accepts a male audio terminal of a cable connected to an audio source. Additionally or alternatively, auxiliary audio input 502 may include and/or represent a wireless communication receiver and/or transceiver that wirelessly interfaces with a wireless communication transmitter and/or transceiver of an audio source. Exemplary audio sources include, but are not limited to, streaming audio outputs or devices, telephone audio outputs or devices, assisted-listening systems or devices, variations of one or more of the same, combinations of one or more of the same, and/or any other suitable audio sources as may serve a particular implementation.

In one example, control module 202 may be further communicatively coupled to auxiliary audio input 502. In this example, auxiliary audio input 502 may receive incoming auxiliary audio from the audio source, and control module 202 may provide the incoming auxiliary audio received by auxiliary audio input 502 to body-worn sound processor apparatus 104 by way of cable 302. By providing the incoming auxiliary audio to body-worn sound processor apparatus 104 in this way, control module 202 may enable body-worn sound processor apparatus 104 to generate an additional control parameter that controls an operation of cochlear implant 108 and then transmit, by way of cables 302 and 308 and communication ports 204 and 206, the additional control parameter to headpiece 106 for wireless transmission to cochlear implant 108.

Figure 6:
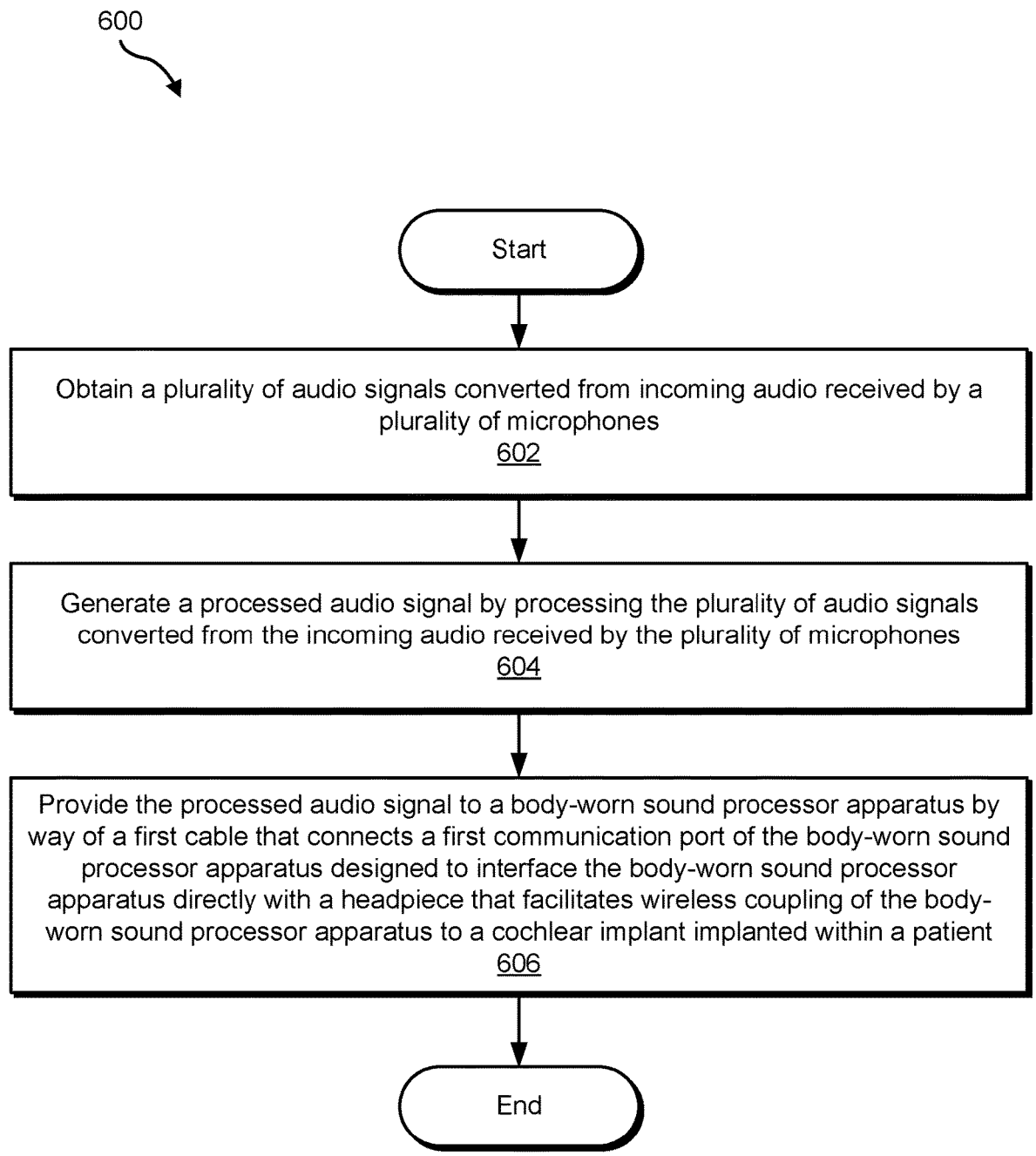
FIG. 6 illustrates an exemplary method according to principles described herein.

FIG. 6 illustrates an exemplary method 600. While FIG. 6 illustrates exemplary steps according to one embodiment, other embodiments may omit, add to, reorder, and/or modify any of the steps shown in FIG. 6. One or more of the steps shown in FIG. 6 may be performed by control module 202 of audio accessory 116 and/or any implementation thereof.

In step 602, a control module included within an audio accessory associated with a patient may obtain a plurality of audio signals converted from incoming audio received by a plurality of microphones. Step 602 may be performed in any of the ways described herein.

In step 604, the control module may generate a processed audio signal by processing the plurality of audio signals converted from the incoming audio received by the plurality of microphones. Step 604 may be performed in any of the ways described herein.

In step 606, the control module may provide the processed audio signal to a body-worn sound processor apparatus by way of a first cable that connects a first communication port of the body-worn sound processor apparatus designed to interface the body-worn sound processor apparatus directly with a headpiece that facilitates wireless coupling of the body-worn sound processor apparatus to a cochlear implant implanted within the patient. By providing the processed audio signal to the body-worn sound processor apparatus in this way, the control module may enable the body-worn sound processor apparatus to generate a control parameter that controls an operation of the cochlear implant. The body-worn sound processor apparatus may then transmit the control parameter to the headpiece for wireless transmission to the cochlear implant by way of the first cable and a second cable that connects a communication port of the headpiece designed to interface the headpiece directly with the body-worn sound processor apparatus. Step 606 may be performed in any of the ways described herein.

In the preceding description, various exemplary embodiments have been described with reference to the accompanying drawings. It will, however, be evident that various modifications and changes may be made thereto, and additional embodiments may be implemented, without departing from the scope of the invention as set forth in the claims that follow. For example, certain features of one embodiment described herein may be combined with or substituted for features of another embodiment described herein. The description and drawings are accordingly to be regarded in an illustrative rather than a restrictive sense.

What is claimed is:

1. An auditory prosthesis system comprising:
    a body-worn sound processor apparatus configured to be external to a patient and control an operation of a cochlear implant implanted within the patient;
    a headpiece configured to be external to the patient and facilitate wireless coupling of the body-worn sound processor apparatus to the cochlear implant;
    an audio accessory configured to be external to the patient and that includes
        a microphone configured to receive incoming audio and convert the incoming audio into an audio signal;
        a first communication port configured to connect directly to a communication port of the body-worn sound processor apparatus by way of a first cable;
        a second communication port configured to connect directly to a communication port of the headpiece by way of a second cable, the communication port of the headpiece designed to interface the headpiece directly with the body-worn sound processor apparatus; and
        a control module communicatively coupled to the microphone and the first and second communication ports and that is configured to provide the audio signal to the body-worn sound processor apparatus by way of the first cable;
    wherein the body-worn sound processor is configured to generate, based on the audio signal, a control parameter; and
    transmit, by way of the first and second cables and the first and second communication ports, the control parameter to the headpiece for wireless transmission to the cochlear implant; and
    wherein the communication port of the body-worn sound processor apparatus comprises a headpiece-interface port designed to receive an audio signal from a microphone included in the headpiece and transmit data directly to the headpiece for wireless transmission to the cochlear implant.

2. The auditory prosthesis system of claim 1, wherein the audio accessory is removably interposed between the body-worn sound processor apparatus and the headpiece by:

connecting the first communication port to the communication port of the body-worn sound processor apparatus by way of the first cable despite the communication port of the body-worn sound processor being designed to interface the body-worn sound processor apparatus directly with the headpiece; and connecting the second communication port to the communication port of the headpiece by way of the second cable despite the communication port of the body-worn sound processor being designed to interface the body-worn sound processor apparatus directly with the headpiece.

3. The auditory prosthesis system of claim 2, wherein the audio accessory is removed such that the body-worn sound processor apparatus interfaces directly with the headpiece by way of the first cable or the second cable connecting the communication port of the body-worn sound processor apparatus directly to the communication port of the headpiece.

4. The auditory prosthesis system of claim 1, wherein the first cable, despite facilitating a direct connection between the first communication port and the communication port of the body-worn sound processor apparatus, is designed to connect the body-worn sound processor apparatus directly to the headpiece.

5. The auditory prosthesis system of claim 1, wherein the second cable, despite facilitating a direct connection between the second communication port and the communication port of the headpiece, is designed to connect the body-worn sound processor apparatus directly to the headpiece.

6. The auditory prosthesis system of claim 1, wherein the first cable comprises a radio-frequency cable.

7. The auditory prosthesis system of claim 1, wherein, prior to providing the audio signal to the body-worn sound processor, the control module is configured to perform a beamforming operation on the audio signal to remove unwanted noise.

8. The auditory prosthesis system of claim 1, wherein the microphone comprises a plurality of microphones.

9. The auditory prosthesis system of claim 1, wherein the communication port of the body-worn sound processor apparatus is designed to interface the body-worn sound processor apparatus directly with the headpiece.

10. The auditory prosthesis system of claim 1, wherein:
the audio accessory further includes an auxiliary audio input configured to receive incoming auxiliary audio;
the control module is further communicatively coupled to the auxiliary audio input and is further configured to provide the incoming auxiliary audio received by the auxiliary audio input to the body-worn sound processor apparatus by way of the first cable; and
the body-worn sound processor apparatus is further configured to
generate, based at least in part on the incoming auxiliary audio, an additional control parameter that controls the operation of the cochlear implant; and
transmit, by way of the first and second cables and the first and second communication ports, the additional control parameter to the headpiece for wireless transmission to the cochlear implant.

11. An auditory prosthesis system comprising:
a body-worn sound processor apparatus configured to be external to a patient and control an operation of a cochlear implant implanted within the patient;
a headpiece configured to be external to the patient and facilitate wireless coupling of the body-worn sound processor apparatus to the cochlear implant;
an audio accessory configured to be external to the patient and that includes
a microphone configured to receive incoming audio and convert the incoming audio into an audio signal;
a first communication port configured to connect directly to a communication port of the body-worn sound processor apparatus by way of a first cable; and
a second communication port configured to connect directly to a communication port of the headpiece by way of a second cable, the communication port of the headpiece designed to interface the headpiece directly with the body-worn sound processor apparatus;
an auxiliary audio input configured to receive incoming auxiliary audio; and
a control module communicatively coupled to the microphone, the first and second communication ports, and the auxiliary audio input and that is configured to provide the audio signal and the incoming auxiliary audio to the body-worn sound processor apparatus by way of the first cable;
wherein the body-worn sound processor apparatus is configured to:
generate, based on the audio signal, a control parameter;
generate, based at least in part on the incoming auxiliary audio, an additional control parameter; and
transmit, by way of the first and second cables and the first and second communication ports, the control parameter and the additional control parameter to the headpiece for wireless transmission to the cochlear implant.

12. The auditory prosthesis system of claim 11, wherein the audio accessory is removably interposed between the body-worn sound processor apparatus and the headpiece by:
connecting the first communication port to the communication port of the body-worn sound processor apparatus by way of the first cable despite the communication port of the body-worn sound processor being designed to interface the body-worn sound processor apparatus directly with the headpiece; and
connecting the second communication port to the communication port of the headpiece by way of the second cable despite the communication port of the body-worn sound processor being designed to interface the body-worn sound processor apparatus directly with the headpiece.

13. The auditory prosthesis system of claim 11, wherein the first cable, despite facilitating a direct connection between the first communication port and the communication port of the body-worn sound processor apparatus, is designed to connect the body-worn sound processor apparatus directly to the headpiece.

14. An auditory prosthesis system comprising:
an audio accessory configured to be external to a patient and that includes
a microphone that receives incoming audio and converts the incoming audio into an audio signal;
a first communication port that connects directly to a communication port of the body-worn sound processor apparatus by way of a first cable;
a second communication port that connects directly to a communication port of the headpiece by way of a second cable, the communication port of the headpiece designed to interface the headpiece directly with the body-worn sound processor apparatus; and a control module communicatively coupled to the microphone and the first and second communication ports and that provides the audio signal to the body-worn sound processor apparatus by way of the first cable;

wherein the body-worn sound processor is further configured to generate, based on the audio signal, a control parameter; and transmit, by way of the first and second cables and the first and second communication ports, the control parameter to the headpiece for wireless transmission to the cochlear implant; and wherein the communication port of the body-worn sound processor apparatus comprises a headpiece-input port designed to receive an audio signal from a microphone included in the headpiece and transmit data directly to the headpiece for wireless transmission to the cochlear implant.

15. The auditory prosthesis system of claim 14, wherein the audio accessory is removably interposed between the body-worn sound processor apparatus and the headpiece by:

connecting the first communication port to the communication port of the body-worn sound processor apparatus by way of the first cable despite the communication port of the body-worn sound processor being designed to interface the body-worn sound processor apparatus directly with the headpiece; and connecting the second communication port to the communication port of the headpiece by way of the second cable despite the communication port of the body-worn sound processor being designed to interface the body-worn sound processor apparatus directly with the headpiece.

16. The auditory prosthesis system of claim 15, wherein the audio accessory is removed such that the body-worn sound processor apparatus interfaces directly with the headpiece by way of the first cable or the second cable connecting the communication port of the body-worn sound processor apparatus directly to the communication port of the headpiece.

17. The auditory prosthesis system of claim 14, wherein the first cable, despite facilitating a direct connection between the first communication port and the communication port of the body-worn sound processor apparatus, is designed to connect the body-worn sound processor apparatus directly to the headpiece.

18. The auditory prosthesis system of claim 14, wherein the second cable, despite facilitating a direct connection between the second communication port and the communication port of the headpiece, is designed to connect the body-worn sound processor apparatus directly to the headpiece.

19. The auditory prosthesis system of claim 14, wherein the first cable comprises a radio-frequency cable.

20. The auditory prosthesis system of claim 14, wherein the control module generates the processed audio signal by performing a beamforming operation on the audio signal to remove unwanted noise.

* * * * *